United States Patent
Davis et al.

(10) Patent No.: US 11,883,313 B2
(45) Date of Patent: Jan. 30, 2024

(54) HEEL FLOAT THERAPEUTIC FOOTWEAR

(71) Applicant: Osborn Medical Corp., Centennial, CO (US)

(72) Inventors: William D. Davis, Denver, CO (US); Ian P. MacDonald, Denver, CO (US)

(73) Assignee: Osborn Medical Corp., Centennial, CO (US)

( * ) Notice: Subject to any disclaimer, the term of this patent is extended or adjusted under 35 U.S.C. 154(b) by 0 days.

(21) Appl. No.: 17/681,463

(22) Filed: Feb. 25, 2022

(65) Prior Publication Data
US 2022/0362046 A1  Nov. 17, 2022

Related U.S. Application Data

(63) Continuation of application No. 16/743,087, filed on Jan. 15, 2020, now Pat. No. 11,285,030, which is a continuation of application No. 15/271,459, filed on Sep. 21, 2016, now Pat. No. 10,575,978, which is a continuation of application No. 13/622,829, filed on Sep. 19, 2012, now Pat. No. 9,615,958.

(51) Int. Cl.
*A61F 5/01* (2006.01)
*A61F 5/058* (2006.01)
*A61F 5/37* (2006.01)
*A61F 13/06* (2006.01)

(52) U.S. Cl.
CPC .......... *A61F 5/0111* (2013.01); *A61F 5/0585* (2013.01); *A61F 5/37* (2013.01); *A61F 13/064* (2013.01); *A61F 5/019* (2013.01)

(58) Field of Classification Search
CPC .................................................... A61F 5/0585
See application file for complete search history.

(56) References Cited

U.S. PATENT DOCUMENTS

| | | | |
|---|---|---|---|
| 3,804,085 A | 4/1974 | Eshuis et al. |
| 5,143,058 A | 9/1992 | Luber et al. |
| 5,226,245 A | 7/1993 | Lamont |
| 5,486,157 A | 1/1996 | DiBenedetto |
| 5,718,673 A | 2/1998 | Shipstead |
| 5,762,622 A | 6/1998 | Lamont |
| 5,860,423 A | 1/1999 | Thompson |

(Continued)

OTHER PUBLICATIONS

Rooke® Heel Float System; http://www.piersonsurgical.com/rooke.html; dated Jul. 12, 2012; 1 page.

(Continued)

*Primary Examiner* — Tarla R Patel
(74) *Attorney, Agent, or Firm* — Merchant & Gould P.C.

(57) ABSTRACT

A heel float therapeutic footwear for people that spend a large amount of time in bed. The heel float therapeutic footwear includes a lower leg support portion, a foot support portion, and a wing support structure. The foot support portion extends from the lower leg support portion and includes a foot support platform. The wing support structure is permanently attached to the foot support platform. The wing support structure is adjustably fastenable to a side of the lower leg support portion to adjustably support a position and an angle of the foot support platform with respect to the lower leg support portion. A method of making a heel float therapeutic footwear is also disclosed.

18 Claims, 17 Drawing Sheets

(56) References Cited

U.S. PATENT DOCUMENTS

| | | | |
|---|---|---|---|
| 5,876,364 | A | 3/1999 | Herbst |
| 6,866,043 | B1 | 3/2005 | Davis |
| 7,798,984 | B2 | 9/2010 | Ponsi et al. |
| 9,615,958 | B2 * | 4/2017 | Davis .................... A61F 13/064 |
| 10,575,978 | B2 * | 3/2020 | Davis .................... A61F 5/0111 |
| 11,285,030 | B2 * | 3/2022 | Davis .................... A61F 13/064 |
| 2009/0084390 | A1 | 4/2009 | Davis et al. |
| 2009/0177132 | A1 | 7/2009 | Reis et al. |
| 2011/0180074 | A1 | 7/2011 | Gainey |
| 2012/0145167 | A1 | 6/2012 | Davis |

OTHER PUBLICATIONS

Rooke® Boots; http://www.woundsource.com/product/rooke-boots; dated Jul. 12, 2012; 2 pages.
Build-a-Boot™; http://www.primoinc.net/Heel_Ulcer_Prevention.php; dated Jul. 12, 2012; 2 pages.
Adjustable Heel Float Boot; http://www.mountainside-medical.com/products/Adjustable-Heel-Float-Boot.html; dated Jul. 12, 2012; 2 pages.
HeelPro Heel Protector; http://www.talarmade.com/products/567-heelpro-heel-protector.aspx; dated Jul. 12, 2012; 1 page.
Herbst Cradle™ Ankle Foot Orthoses; https://wdms.medline.com/heel-and-elbow/ankle-contracture-boots.asp; dated Jul. 12, 2012; 1 page.

* cited by examiner

HEEL FLOAT THERAPEUTIC FOOTWEAR

CROSS-REFERENCE TO RELATED APPLICATIONS

This application is a Continuation of U.S. application Ser. No. 16/743,087, filed on Jan. 15, 2020, titled HEEL FLOAT THERAPEUTIC FOOTWEAR, which is a Continuation of U.S. application Ser. No. 15/271,459 filed on Sep. 21, 2016, titled HEEL FLOAT THERAPEUTIC FOOTWEAR APPARATUS, issued as U.S. Pat. No. 10,575,978, which is a Continuation of U.S. application Ser. No. 13/622,829, titled HEEL FLOAT THERAPEUTIC FOOTWEAR APPARATUS, filed on Sep. 19, 2012, issued as U.S. Pat. No. 9,615,958, the disclosures of which are hereby incorporated by reference in their entireties. To the extent appropriate a claim of priority is made to each of the above-disclosed applications.

BACKGROUND

Hospital patients are sometimes bed ridden for long periods of time. In some situations the patient can experience problems associated from lying down in one position for so long. For example, patients with vascular disease need to have good blood circulation to prevent clotting. The proper pre and post-operative footwear is needed to prevent vasoconstriction and promote vasodilation. In addition to maintaining proper blood circulation, the foot must be prevented from pointing in the downward direction or leaning to the side, a problem recognized in the industry that can lead to foot drop. Foot drop is a condition that may occur after lying in bed for some time without getting up or walking. Foot drop is the dropping of the forefoot due to weakness, damage to the peroneal nerve or paralysis of the muscles in the anterior portion of the lower leg. It is characterized by the inability or difficulty in moving the ankle and toes upward and thereby leading to the improper rotation of the foot. Heel or foot ulcers are another condition that can develop as a result of the heel rubbing against the pre or post-operative footwear or pressure being placed on the heel while lying in a hospital bed.

SUMMARY

In general terms, this disclosure is directed to a heel float therapeutic footwear apparatus. In one possible configuration, and by non-limiting example, a heel float therapeutic footwear apparatus includes a lower leg support portion, a foot support portion, and a wing support structure.

One aspect is a heel float therapeutic footwear apparatus comprising: a lower leg support portion; a foot support portion extending from the lower leg support portion; the foot support portion including a foot support platform; and a wing support structure permanently attached at a first end portion to the foot support platform, and having a second end portion that is adjustably fastenable to a side of the lower leg support portion.

Another aspect is a heel float therapeutic footwear apparatus comprising: a lower leg support portion configured to support a lower leg of a patient, the lower leg support portion including a lower leg support cradle having a raised portion, the raised portion configured to elevate a heel of the patient when the patient is lying on the patient's back to reduce pressure on the patient's heel; a foot support portion connected to and extending from the lower leg support portion; the foot support portion including a foot support platform extending from the lower leg support cradle; and a wing support structure having a first end portion and a second end portion, the wing support structure permanently attached to the foot support platform at the first end portion, and being adjustably fastenable at the second end portion to a side of the lower leg support portion to adjustably support a position and an angle of the foot support platform with respect to the lower leg support portion.

A further aspect is a method of making a heel float therapeutic footwear apparatus, the method comprising: forming a lower leg support portion and a foot support portion, the foot support portion including a foot support platform; forming a wing support structure including a left support wing and a right support wing, each of the wings including a first end portion and a second end portion, wherein the second end portions are configured to be adjustably fastened to opposite sides of the lower leg support portion; and permanently fastening the first end portions of the left and right support wings to the foot support portion.

DETAILED DESCRIPTION

Figure 1:
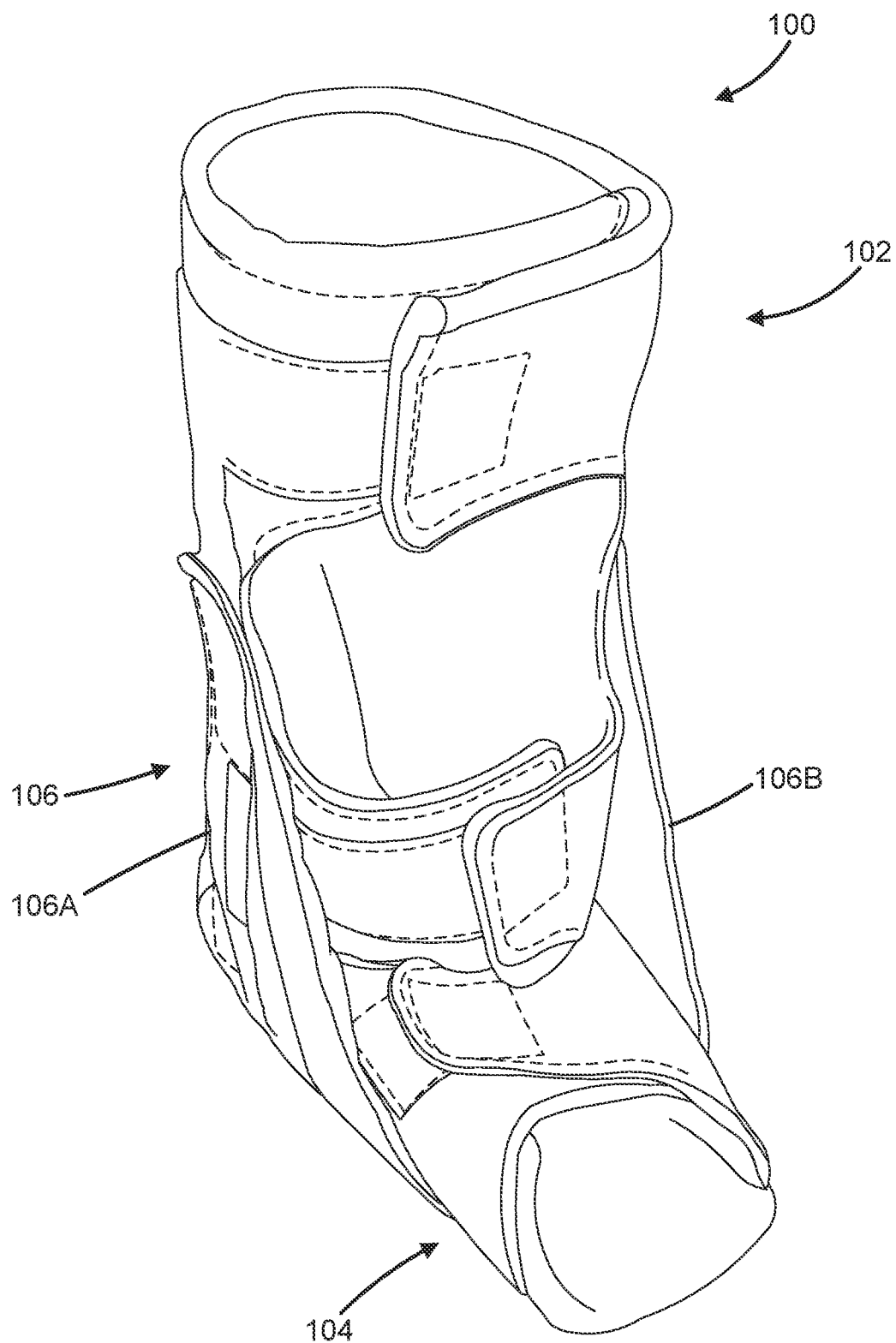
FIG. 1 is perspective view of an example of a heel float therapeutic boot with a wing support structure fastened in accordance with the principles of the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Figure 2:
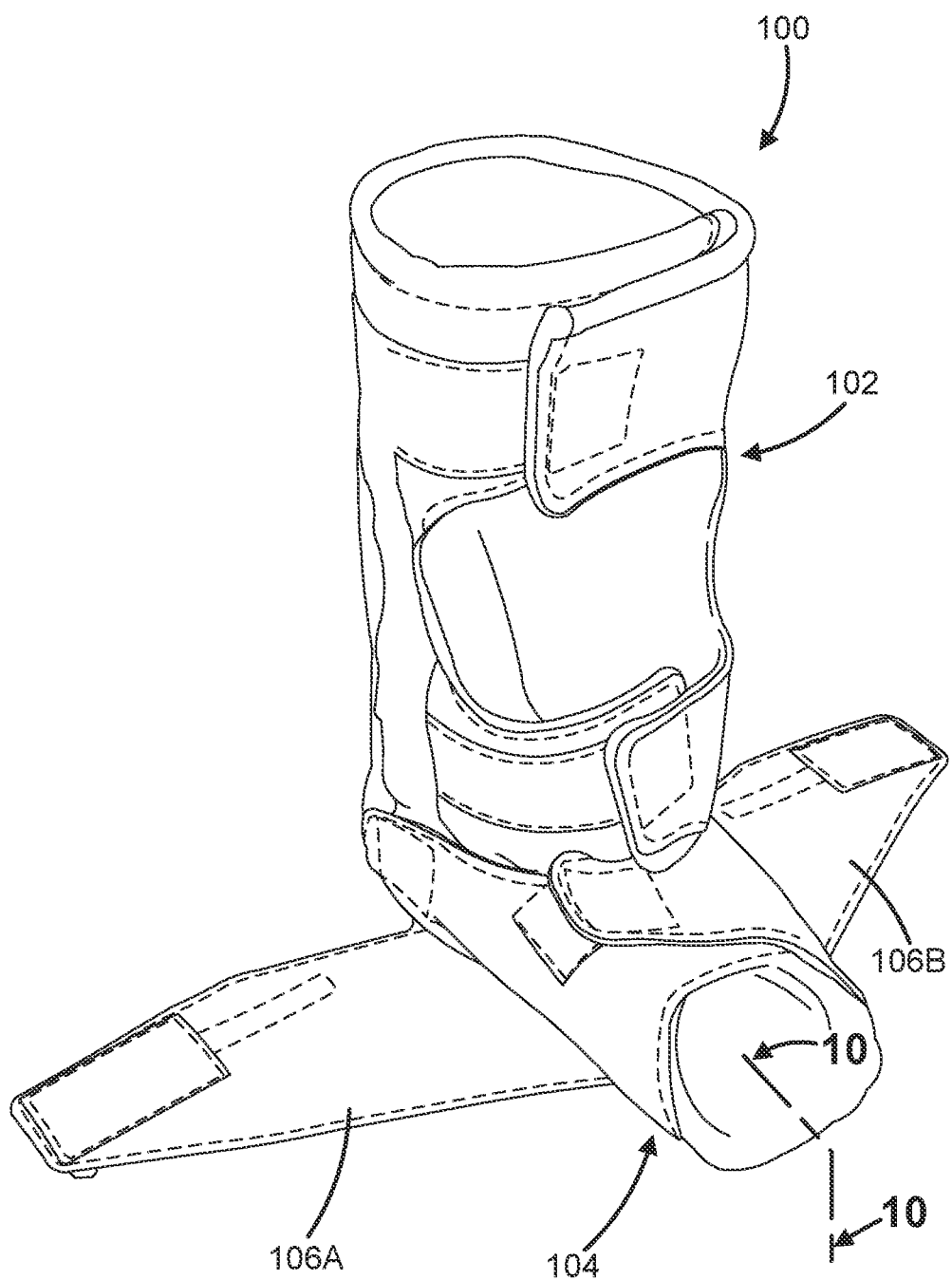
FIG. 2 is perspective view of the heel float therapeutic boot shown in FIG. 1 with the wing support structure unfastened.

FIGS. 1-2 are perspective views of an example of a heel float therapeutic boot 100. In this example, the heel float therapeutic boot 100 includes a lower leg support portion 102, a foot support portion 104, and a wing support structure 106. In FIG. 1, the wing support structure 106 are configured as being attached to the heel float therapeutic boot 100. In FIG. 2, the wing support structure 106 is shown as being open and unfastened to the heel float therapeutic boot 100.

The heel float therapeutic boot 100 can be worn by hospital patients to help support the foot of a patient and off-load weight from the heel of the patient. The heel float therapeutic boot 100 may help to prevent foot drop by keeping the foot in an upright position thereby preventing the foot from falling over to one side or from pointing toward the foot of the bed while lying down. The heel float therapeutic boot 100 can also be used to elevate the heel so that it does not rub on the bottom of the boot or on the padding. The heel float therapeutic boot 100 supports the foot in a preferred position.

The lower leg support portion 102 may be considered the main body of the heel float therapeutic boot 100 and typically covers the lower leg portion of a patient's leg including at least a portion of the calf and ankle. The lower leg support portion 102 helps protect against pressure ulcers formed on the skin and keeps the legs warm. The lower leg support portion is illustrated and described in more detail with reference to FIGS. 3-7.

The foot support portion 104 of the heel float therapeutic boot 100 extends adjacent to the lower leg support portion 102 and covers portions of the foot area. The foot support portion 104 helps protect against pressure ulcers formed on the skin and keeps the feet warm. In some embodiments, the foot support portion 104 is connected to the lower leg support portion 102 creating a hinge between the two. The foot support portion 104 is illustrated and described in more detail with reference to FIGS. 8-12.

The wing support structure 106 of the heel float therapeutic boot 100 supports the foot in a preferred position. The wing support structure 106 is attached to the heel float therapeutic boot 100 and is configured to be adjustable to obtain the preferred position. The wing support structure 106 is illustrated and described in more detail with reference to FIGS. 14-16.

Figure 3:
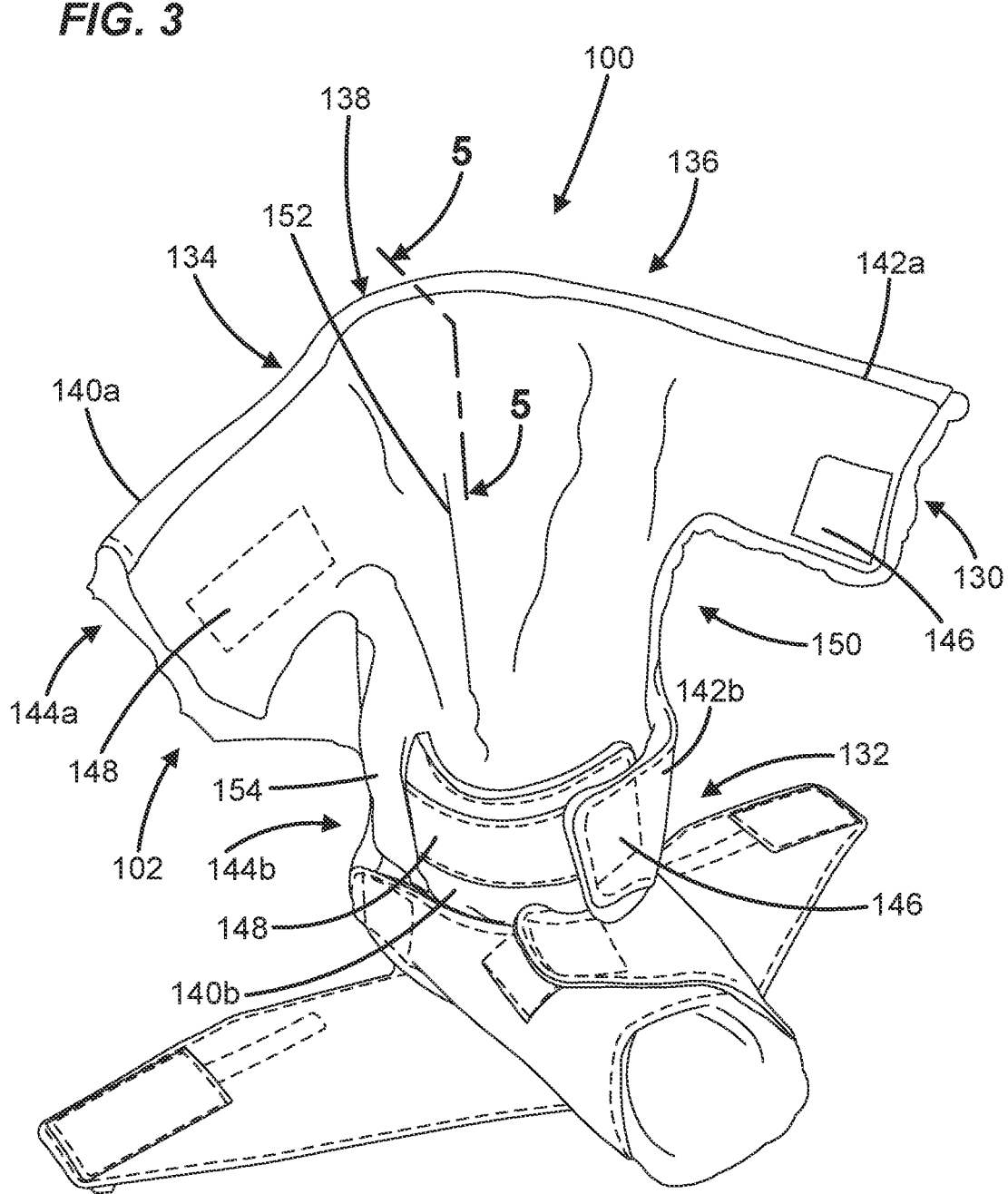
FIG. 3 is a perspective view of the heel float therapeutic boot shown in FIG. 2 with upper overlapping members unfastened.
Figure 4:
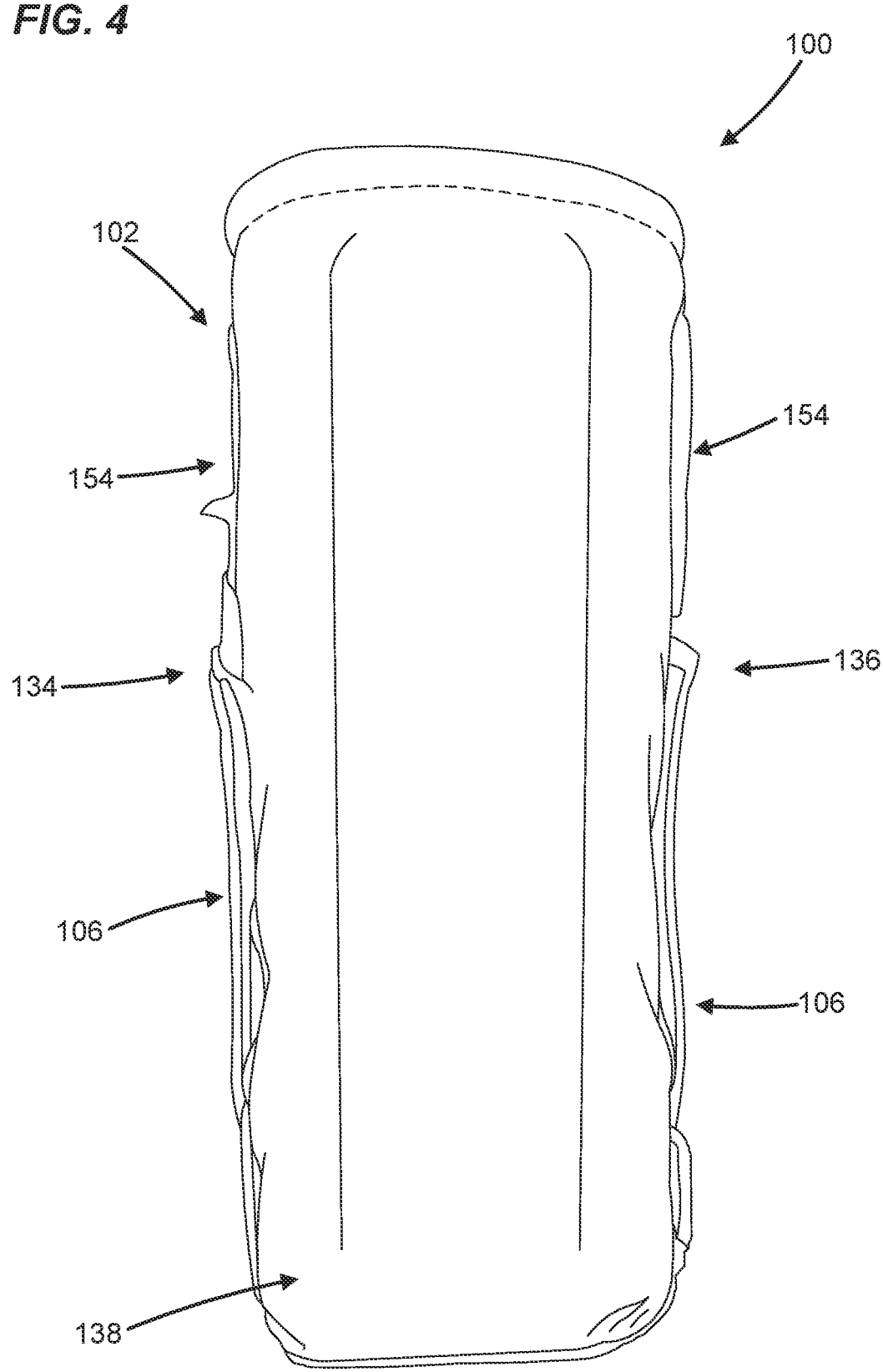
FIG. 4 is a perspective back view of the heel float therapeutic boot shown in FIG. 1.
Figure 5:
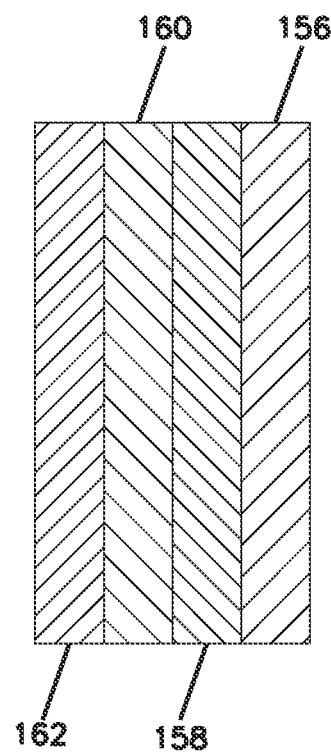
FIG. 5 is a component view of a portion of the heel float therapeutic boot shown in FIG. 3 taken along line 5-5.

FIGS. 3-5 illustrate features of the lower leg support portion 102.

FIGS. 3-4 are perspective front and back views of the lower leg support portion 102. In this example, the lower leg support portion 102 includes an upper overlapping member 130, a lower overlapping member 132, a left side wall 134, a right side wall 136, and a back side wall 138. The lower leg support portion 102 is formed of one piece connecting all of the side walls with both of the overlapping members. The lower leg support portion 102 includes multiple layers that are illustrated and described in detail with reference to FIG. 5.

The upper overlapping member 130 includes a left side panel 140a extending from the left side wall 134 of the lower leg support portion 102 and a right side panel 142a extending from the right side wall 136 of the lower leg support portion 102. The upper overlapping member 130 has a fastening mechanism 144a to connect the left side panel 140a together with the right side panel 142a. In some embodiments, the fastening mechanism 144a includes a hook patch 146 and a loop patch 148. In other embodiments, other fastening mechanisms are used, such as, buttons, adhesive, hooks, clips, clasps, bolts, straps, or combinations of these or other fastening mechanisms. The loop patch 148 is attached to the exterior surface of the left side panel 140a of the upper overlapping member 130 and the hook patch 146 is attached to the right side panel 142a of the upper overlapping member 130. In this example, the hook patch 146 and the loop patch 148 are sewn onto respective panels of the upper overlapping member 130 to be fastened together as the two overlap. In other embodiments, the arrangement and configuration of the hook patch 146 and the loop patch 148 can vary.

The lower overlapping member 132 includes a left side panel 140b extending from the left side wall 134 of the lower leg support portion 102 and a right side panel 142b extending from the right side wall 136 of the lower leg support portion 102. The lower overlapping member 132 has a fastening mechanism 144b to connect the left side panel 140b together with the right side panel 142b. The lower overlapping member 132 may also be provided with a hook patch 146 and a loop patch 148 as the fastening mechanism 144b similar to those described for the upper overlapping member 130. Accordingly, many of the concepts and features for the lower overlapping member 132 are similar to the upper overlapping member 130 previously described herein. In some embodiments, the lower overlapping member 132 is color coded such that the hook patch 146 and loop patch 148 colors are different from other fastening mechanisms, i.e. the upper overlapping member 130. This feature helps to identify for the patient where each overlapping member should be attached if the heel float therapeutic boot 100 becomes crumpled or twisted.

In this example, the upper and lower overlapping members 130, 132 of the lower leg support portion 102 are arranged and configured to wrap and fasten about an anterior portion of the lower leg. In other examples, the lower leg support portion 102 may extend further up the leg. In some embodiments, the upper overlapping member 130 and the lower overlapping member 132 are arranged and configured to define an opening 150 in the front of the lower leg support portion 102 of the heel float therapeutic boot 100. This opening may help provide a cooling feature for the patient when warming is not so critical. It is to be understood that other configurations may be used, such as, but not limited to, a closed configuration having no opening, a slide on boot, or a slip on boot, and combinations of these and other configurations.

Referring to FIG. 4, the left side wall 134 of the lower leg support portion 102 and the right side wall 136 of the lower leg support portion 102 are integrally formed with the back side wall 138 of the lower leg support portion 102 defining a channel 152 (shown in FIG. 3) for receiving a lower leg of a patient. In this example, the left side wall 134 of the lower leg support portion 102 and the right side wall 136 of the lower leg support portion 102 has loop material 154 vertically positioned along the left and right side of the lower leg support portion 102. In this example, the wing support structure 106 is configured to fasten along the loop material 154 positioned on the left and right side of the lower leg support portion 102.

FIG. 5 is a component view of a portion of the heel float therapeutic boot 100 depicting layers of the lower leg support portion 102. In this example, the lower leg support portion 102 includes a fleece material 156, a lining 158, a heel float cradle 160 and exterior fabric 162. The construction and materials used in the heel float therapeutic boot 100 provides the proper support and protection needed for patients.

The fleece material 156 includes the entire lining 158 of the heel float therapeutic boot 100 and is positioned to surround the lower leg of the patient. In this example, the fleece material 156 covers the entire interior of the heel float therapeutic boot 100 to provide for a soft, smooth/comfortable surface to contact the skin without any abrading seams that can cause skin ulcerations. In some embodiments, the fleece material 156 is laminated to the lining 158 of the heel float therapeutic boot 100. In other embodiments, the fleece material 156 can be placed on the lining 158 by other attachment means, such as, adhesive, sewing, or combinations of these or other attachment means.

The lining 158 helps wick moisture away and ventilate the lower leg and foot. Moisture typically develops at regions of sustained contact between the skin and the fleece material 156. In some embodiments, seams can be located between sections of the fleece material 156 and/or lining 158 to minimize contact with the skin. These seams can be sewn or adhesively fixed in the heel float therapeutic boot 100.

The heel float cradle 160 is typically a relatively dense elastic material that flexes or compresses slightly to provide a resilient interface with the lower leg, for example, foam. In this example, the heel float cradle 160 is positioned between the exterior fabric 162 of the heel float therapeutic boot 100 and the lining 158 of the heel float therapeutic boot 100. In some embodiments, the heel float cradle 160 extends along the length of the lower leg support portion 102 and the foot support portion 104. The heel float cradle 160 is illustrated and described in more detail with reference to FIG. 6.

The exterior fabric 162 is constructed of an air permeable material, for example, a durable velour cloth. In some embodiments, other materials such as a heavy weight cotton fabric, CORDURA® or other fabric or fabric combinations might also be used. The exterior fabric 162 covers the entirety of the heel float therapeutic boot 100.

Figure 6:
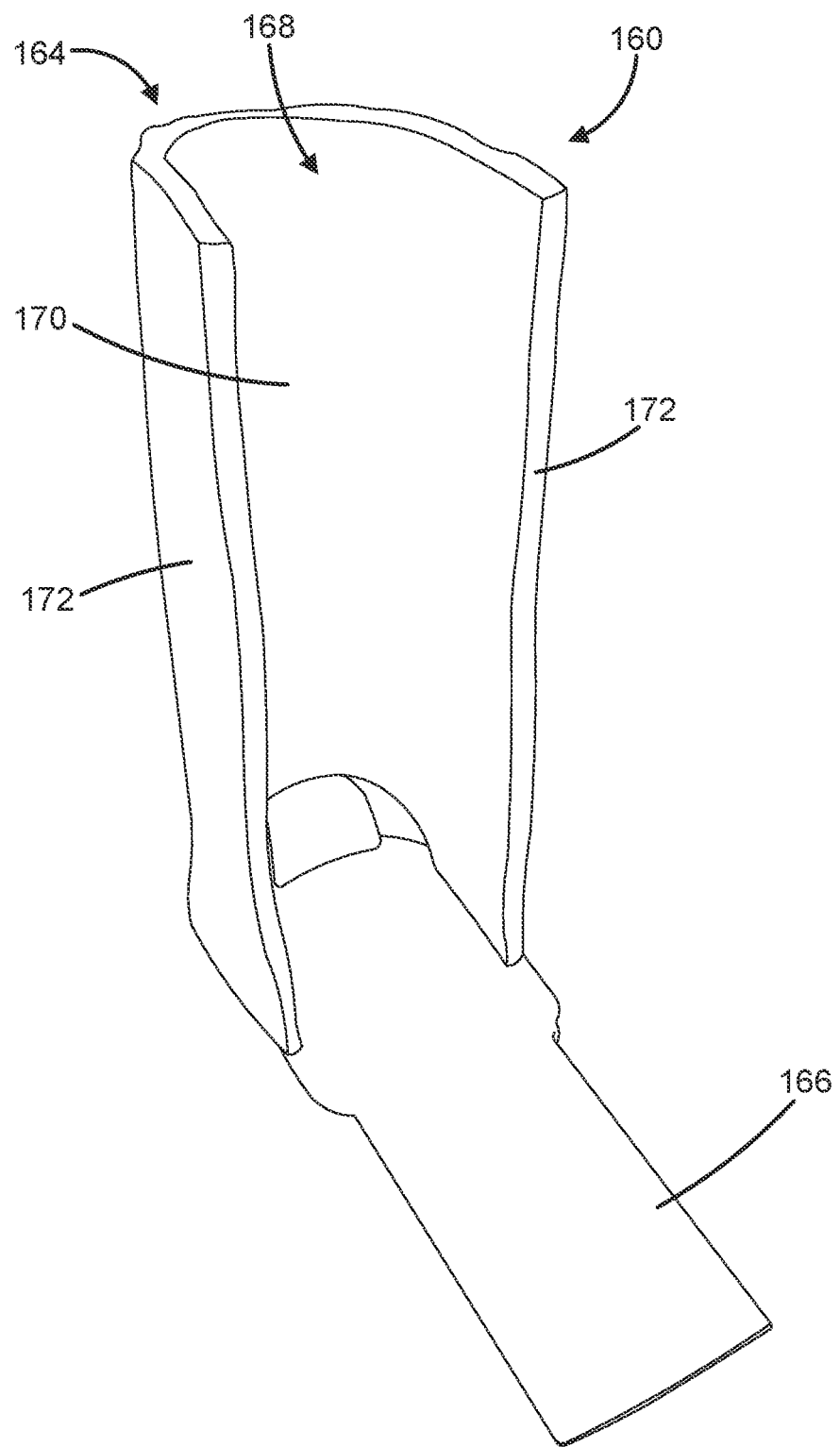
FIG. 6 is a perspective view of an example of a heel float cradle in an upright position in accordance with the principles of the present disclosure.
Figure 7:
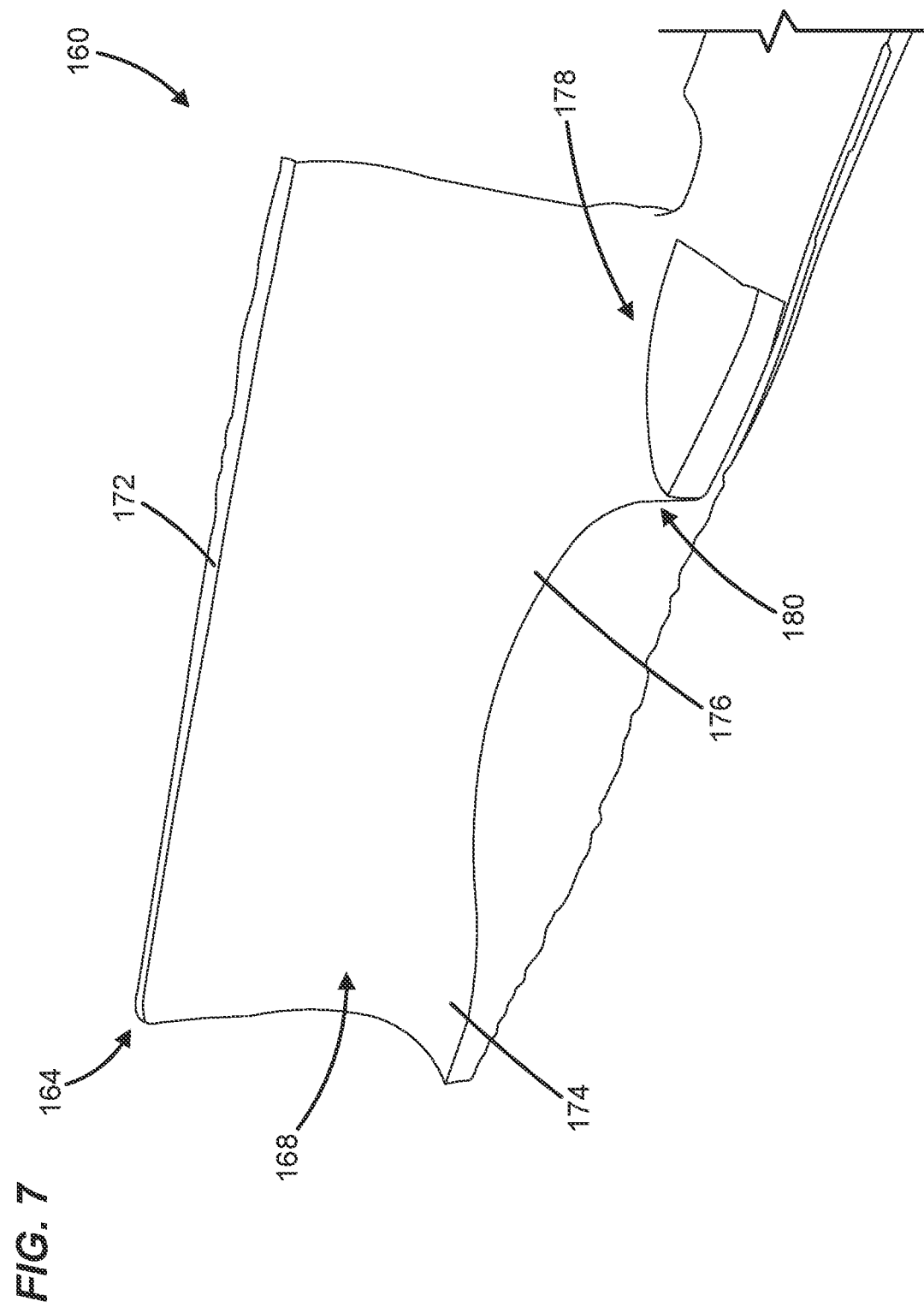
FIG. 7 is a cross-sectional view of a portion of the heel float cradle shown in FIG. 6.

FIGS. 6-7 illustrate features of the heel float cradle 160.

FIG. 6 is a perspective of an example of a heel float cradle 160. In this example, the heel float cradle 160 includes a lower leg support cradle 164 and a foot support platform 166. In this example, the lower leg support cradle 164 and the foot support platform 166 are connected together to form one continuous piece. The heel float cradle 160 can for example be constructed of a variety of materials including elastomers, polyurethane foam, and/or other open and/or closed cell foams or combinations thereof. The durometer and resilience of the material preferably compresses slightly and springs back to shape upon relieving any pressure. The foot support platform 166 is illustrated and described in more detail with reference to FIGS. 11-12.

In this example, the lower leg support cradle 164 includes a posterior flat surface 170 and side walls 172 that extend along the longitudinal sides of the lower leg. The lower leg support cradle 164 provides a longitudinal channel 168 that receives the lower leg of a patient. The posterior flat surface 170 stabilizes the lower leg support cradle 164 and lower leg against rotation when the patient rests in a supine position and the heel float therapeutic boot 100 is supported on a bed. In this example, the lower leg support cradle 164 has a U-shaped cross-section. In other embodiments, the lower leg support cradle 164 has other cross-sectional shapes, such as, a circular shape.

FIG. 7 is a cross-sectional view of the lower leg support cradle 164 of the heel float cradle 160. As shown, the lower leg support cradle 164 includes an anterior surface 174 along the longitudinal channel 168, a raised surface portion 176, a cutout region 178, and a peripheral edge 180 of the anterior surface 174.

In this example, the anterior surface 174 is contoured and exhibits a compound arcuate shape to support the lower leg or calf. The contoured surface helps to distribute and equalize support on the lower leg or calf and prevents pressure points that might induce skin ulcerations or abrasion. The raised surface portion 176 of the anterior surface 174 is in the region of the Achilles tendon and is shaped to elevate and support the heel in the cutout region 178 with minimal pressure and contact with the boot and away from any support structure, such as a bed, foot stool etc. In this example, the cutout region 178 is an inverted U-shape being adjacent to the peripheral edge of the anterior surface 174 of the lower leg support cradle 164. The cutout region 178 is formed to shelter the suspended heel.

Figure 8:
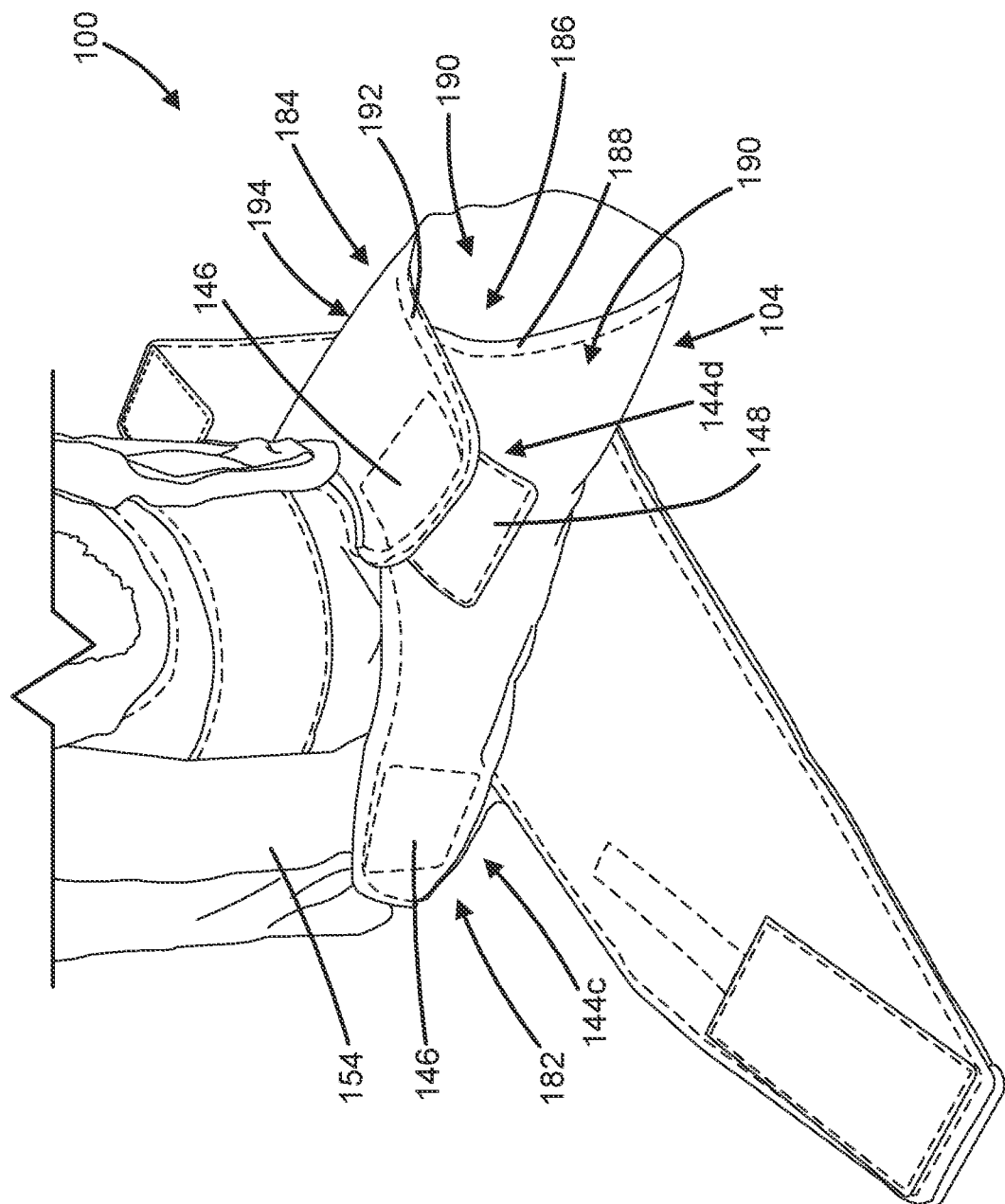
FIG. 8 is a perspective view of a portion of the heel float therapeutic boot shown in FIG. 2.

FIG. 8 is a perspective view of the foot support portion 104 of the heel float therapeutic boot 100. In this example, the foot support portion 104 includes a heel tab 182, an overlapping foot member 184, and a toe opening 186. The heel tab 182 and the overlapping foot member 184 are integrally formed and have separate fastening mechanisms. The heel tab 182 can be detached independent of the overlapping foot member 184 either for inspection or ventilation to expose the heel area. The foot support portion 104 has a length that helps to prevent the foot from popping out underneath or over the top of the foot support portion 104.

In this example, the heel tab 182 has a fastening mechanism 144*c* that connects the heel tab 182 to the loop material 154 vertically positioned along the lower leg support portion 102 of the heel float therapeutic boot 100. The heel tab 182 is arranged and configured on the left and right side of the heel float therapeutic boot 100. The heel tab 182 is also provided with a hook patch 146 similar to those described for the upper and lower overlapping members 130, 132. Accordingly, the description for the hook patch 146 and the loop patch 148 is hereby incorporated by reference in its entirety for the heel tab 182.

The overlapping foot member 184 includes a left side panel 188 extending from a left side wall 190 of the foot support portion 104 and a right side panel 192 extending from a right side wall 194 of the foot support portion 104. In this example, the left and right side panels 188, 192 are integrally formed with the left and right side walls 190, 194 respectively. In some embodiments, the overlapping foot member 184 has moisture wicking material to absorb moisture and ventilate the foot. A variety of soft, moisture absorbent, air permeable open weave or porous materials can be used. The inside of the overlapping foot member 184 that faces the foot is covered with the fleece material 156 similar to the upper and lower overlapping members 130, 132.

The overlapping foot member 184 has a fastening mechanism 144*d* that connects the left side panel 188 together with the right side panel 192. The overlapping foot member 184 may also be provided with a hook patch 146 and a loop patch 148 as the fastening mechanism 144*d* similar to those described for the upper and lower overlapping members 130, 132. Accordingly, many of the concepts and features for the upper and lower overlapping members 130, 132 are similar to the overlapping foot member 184. As such, the description for the hook patch 146 and the loop patch 148 is hereby incorporated by reference in their entirety for the overlapping foot member 184. In some embodiments, the overlapping foot member 184 has a taper configuration that covers a top portion of the foot while leaving an open portion adjacent to the lower leg support portion 102. In other embodiments, the overlapping foot member 184 can cover the entire top of the foot.

In this example, the toe opening 186 is formed by the overlapping foot member 184. The overlapping foot member 184 covers the toes while still providing for ventilation at the toe opening 186.

Figure 9:
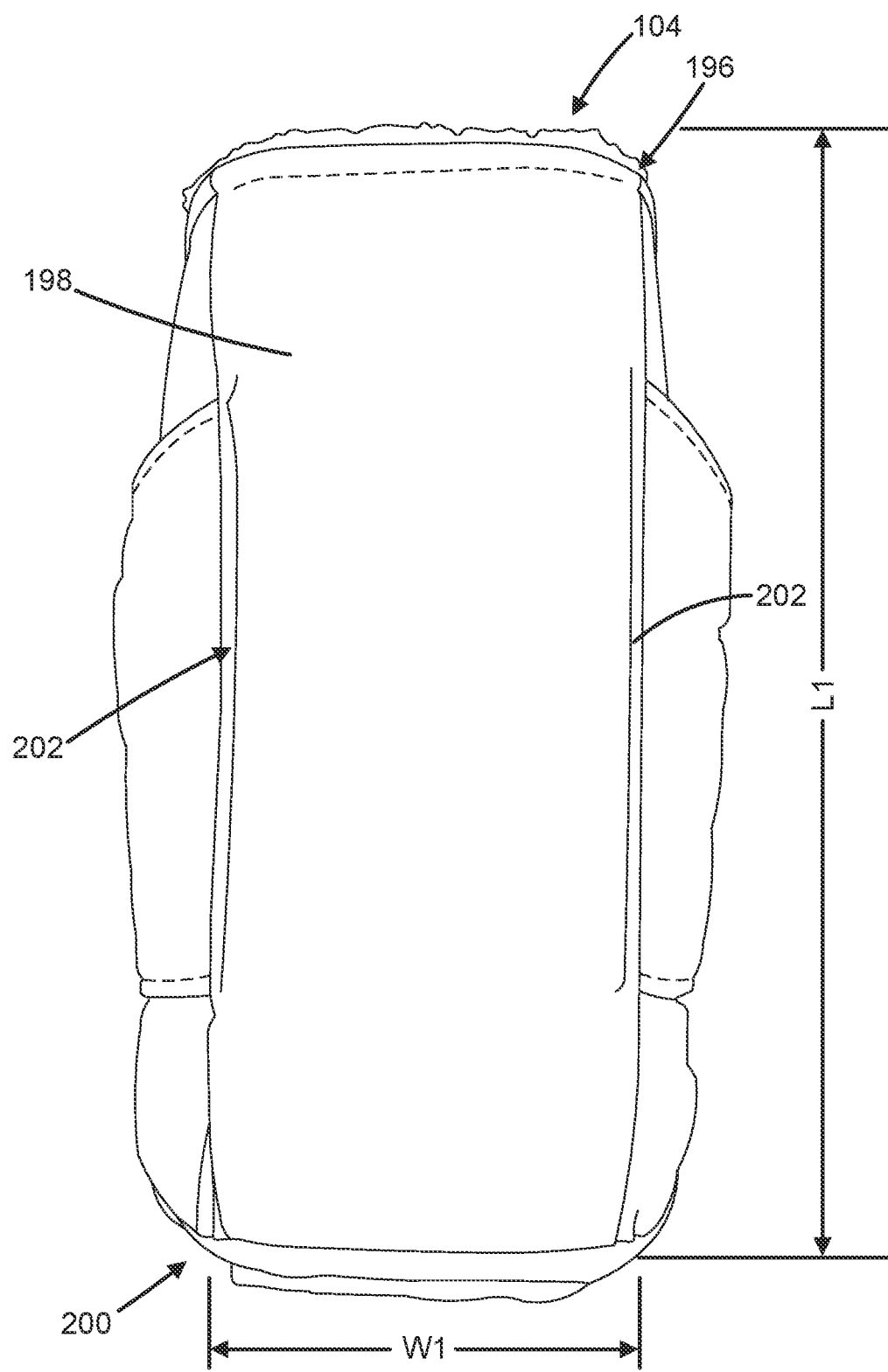
FIG. 9 is a bottom perspective view of the heel float therapeutic boot shown in FIG. 1.

FIG. 9 is a bottom perspective view illustrating exemplary features of the foot support portion 104. In the illustrated example, the foot support portion 104 includes a base 196, a grip material 198, and a flexible hinge 200. The base 196 of the foot support portion 104 has a length L1 and a width W1. In this example, the base 196 of the foot support portion 104 extends beyond the location of the overlapping foot member 184 that covers the toes. The base 196 of the foot support portion 104 extends past the toes and acts as a stub which can help to protect the patient while shuffling along a floor.

The grip material 198 covers the entire base 196 of the foot support portion 104. The grip material 198 acts as a non-slip material to facilitate safe ambulation over smooth tile or wood floors. The grip material 198 can be constructed of a variety of non-slip materials and is shaped to essentially align with and underlie the base 196 of the foot support portion 104. The grip material 198 includes longitudinal sides 202 that extend the length L1 of the base 196. The grip material 198 is attached to the exterior fabric 162 along the longitudinal sides 202 in the region of the sole. In this example, the grip material 198 is sewn to the exterior fabric 162 of the heel float therapeutic boot 100. Other attachment mechanism may be used, such as, but not limiting to, lamination.

The flexible hinge 200 is formed at the location where the lower leg support portion 102 and the foot support portion 104 are connected together.

Figure 10:
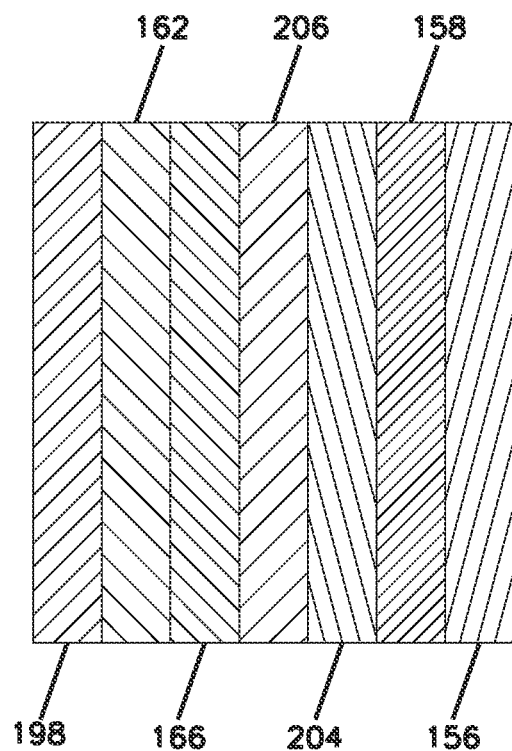
FIG. 10 is a component view of a portion of the heel float therapeutic boot shown in FIG. 2 taken along line 10-10.

FIG. 10 is a component view of a portion of the foot support portion 104 depicting layers of material therein. In this example, the foot support portion 104 includes a fleece material 156, a lining 158, a foam layer 204, an interior fabric 206, the foot support platform 166, the exterior fabric 162, and the grip material 198. As noted above, the foot support platform 166 is illustrated and described in more detail with reference to FIG. 11. The construction of multiple layers provides a more firm platform for the foot to rest against. The foam layer 204 provides for more cushion to the foot and reduces pressure thereon. The interior fabric 206 is of a type similar to the exterior fabric 162 but rather lined inside portions of the heel float therapeutic boot 100. Many of the concepts and features for these layers have been disclosed or are similar to the lower leg support portion 102 shown in FIG. 5. Accordingly, the descriptions of these layers are hereby incorporated by reference in their entirety for the foot support portion 104.

Figure 11:
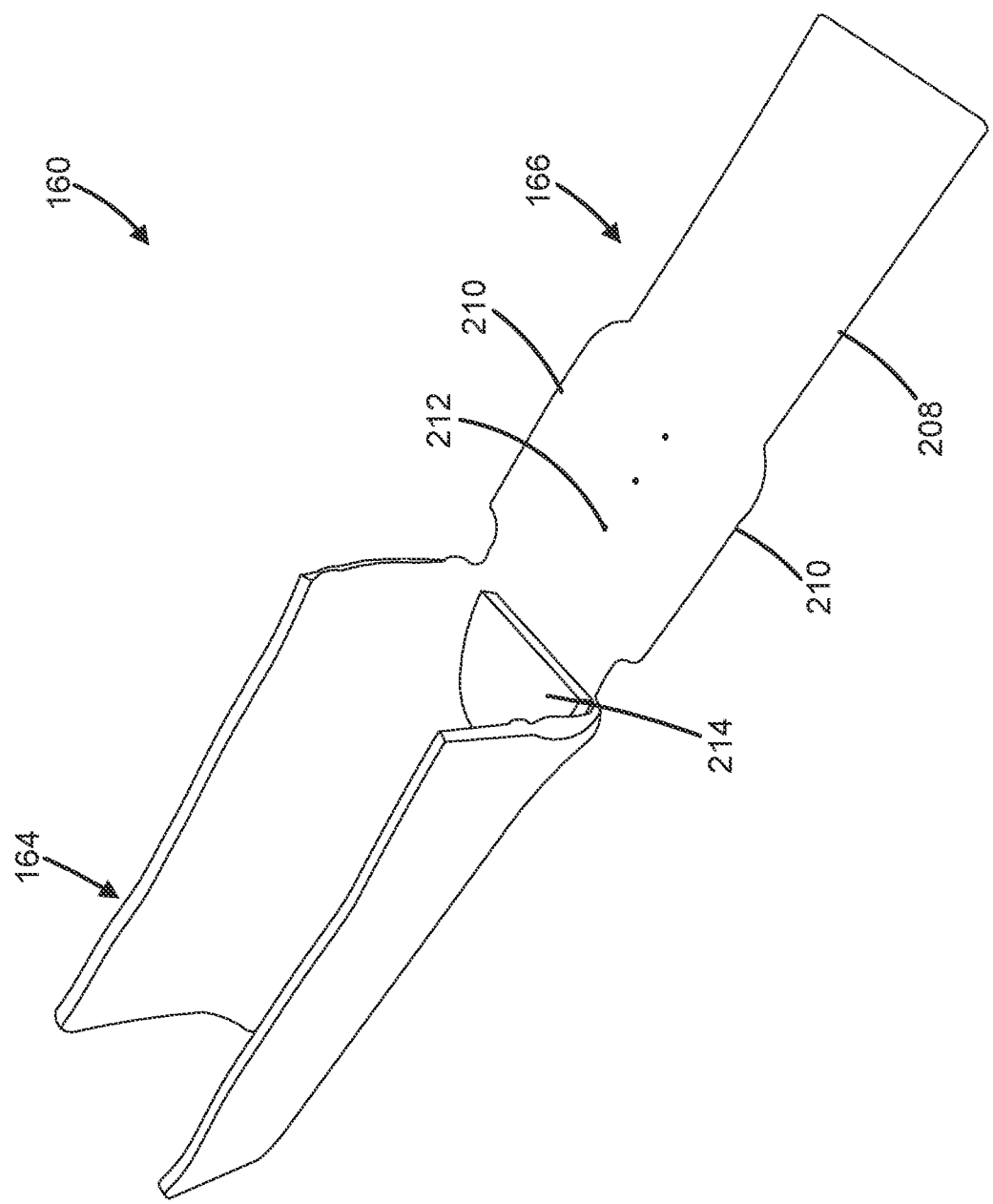
FIG. 11 is a perspective view of the heel float cradle shown in FIG. 6 without being in an upright position.
Figure 12:
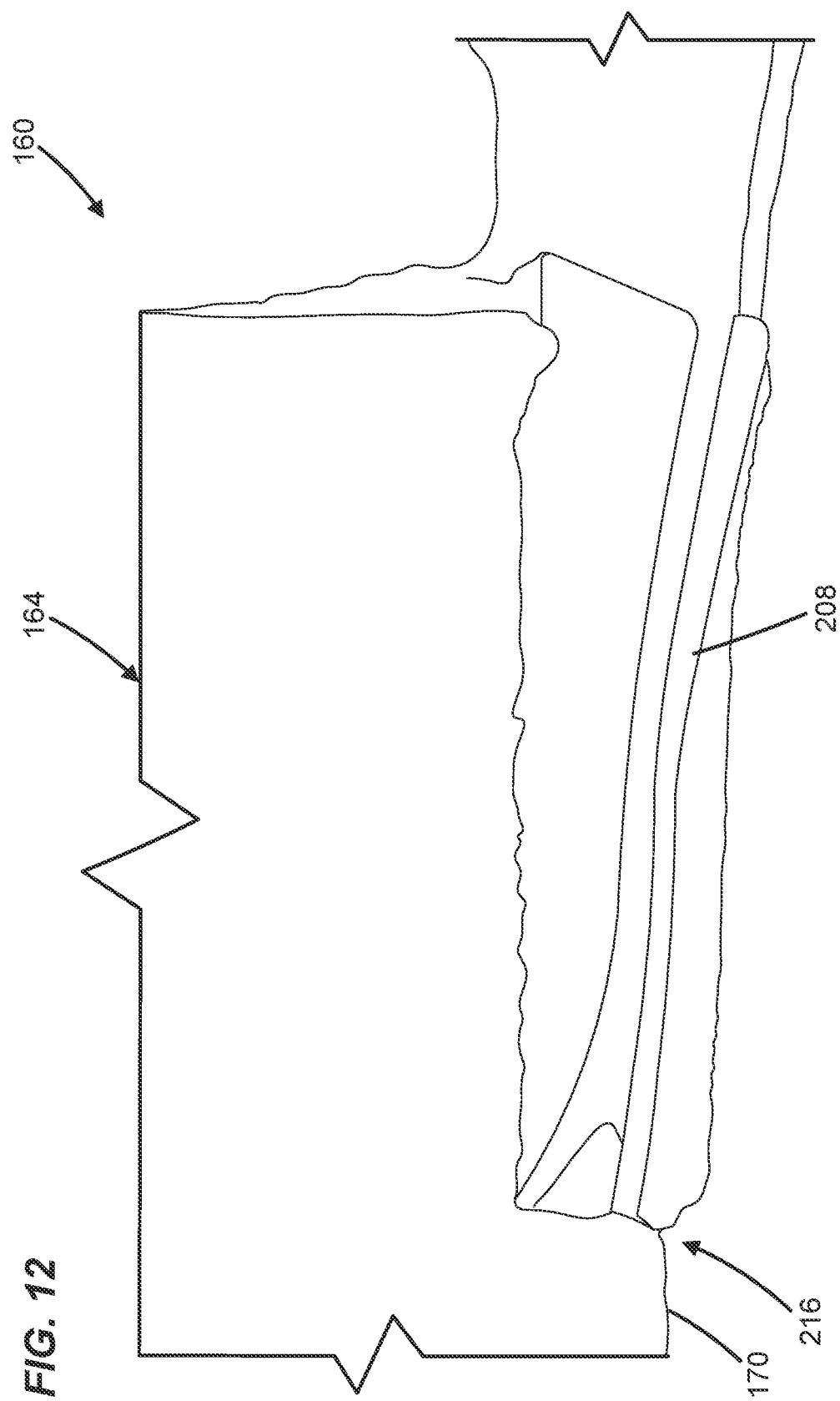
FIG. 12 is an enlarged view of a portion of the heel float cradle shown in FIG. 11.

FIGS. 11-12 illustrate features of the foot support platform 166 of the heel float cradle 160.

FIG. 11 is a perspective view of the foot support platform 166 of the heel float cradle 160. In this example, the foot support platform 166 includes an extended flap portion 208, flaps 210, apertures 212, and foam 214.

The extended flap portion 208 is arranged and configured to align with the base 196 of the foot support portion 104. In this example, the extended flap portion 208 is constructed of closed cell foam, approximately ⅛-inch thick. In other embodiments, the thickness of the extended flap portion 208 can be greater or less. A proximal end of the extended flap portion 208 is bonded to a recess 216 (depicted in FIG. 12) formed into the posterior flat surface 170 of the lower leg support cradle 164 adjacent an inverted U-shaped cutout region 178 being adjacent to the peripheral edge of the anterior surface 174 of the lower leg support cradle 164. The lower leg support cradle 164 and the foot support platform 166 are married together at the recess 216 to create the hinge 200 point in the heel float therapeutic boot 100. The extended flap portion 208 includes apertures 212 to aerate the foot.

The flaps 210 extend from opposite sides of the extended flap portion 208. The flaps 210 are joined with the other layers in the foot support portion 104. In this example, the wing support structure 106 leverages support from the flaps 210 while being adjustably fastened as desired. The wing support structure 106 is illustrated and described in more detail with reference to FIGS. 14-16. The layers of the foot support portion 104 are attached together along the flaps 210 in the region of the sole. In this example, the layers are sewn together through the flaps 210.

The foam 214 is positioned on the extended flap portion 208 at the proximal end below the raised heel. The foam 214 is below the cutout region 178 and provides the cushion for the patient's heel. In this example, the foam 214 is shaped as a half moon. In other embodiments, the foam 214 can take the form of other shapes, such as, circles, square, or rectangular etc.

Figure 13:
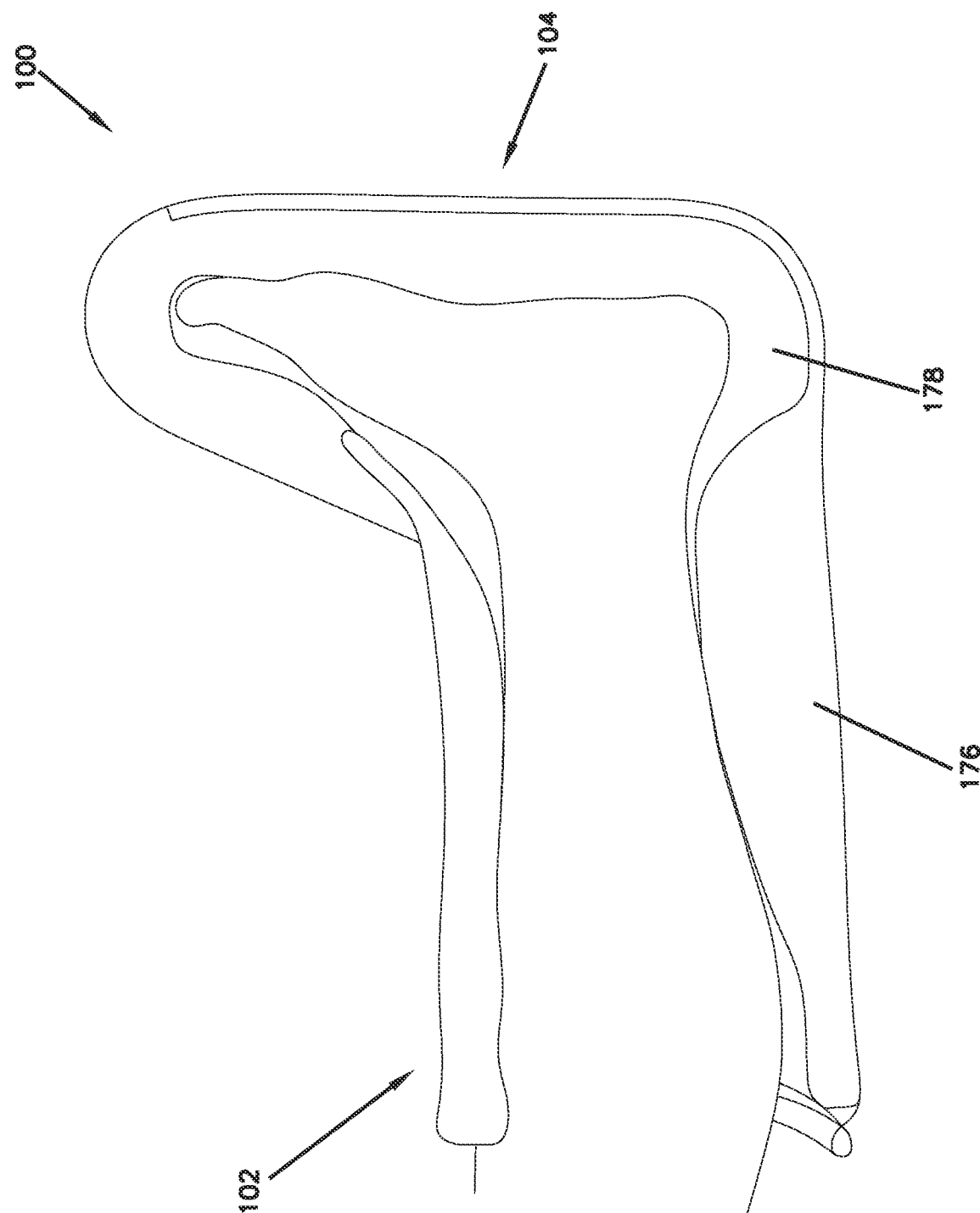
FIG. 13 is a cross-sectional view of the heel float therapeutic boot shown in FIG. 1 with a lower leg of a patient.

FIG. 13 depicts a cross-sectional view of an example of a patient's foot in the heel float therapeutic boot 100. In this example, the heel is shown elevated with the foot positioned upright at approximately 90 degrees.

Figure 14:
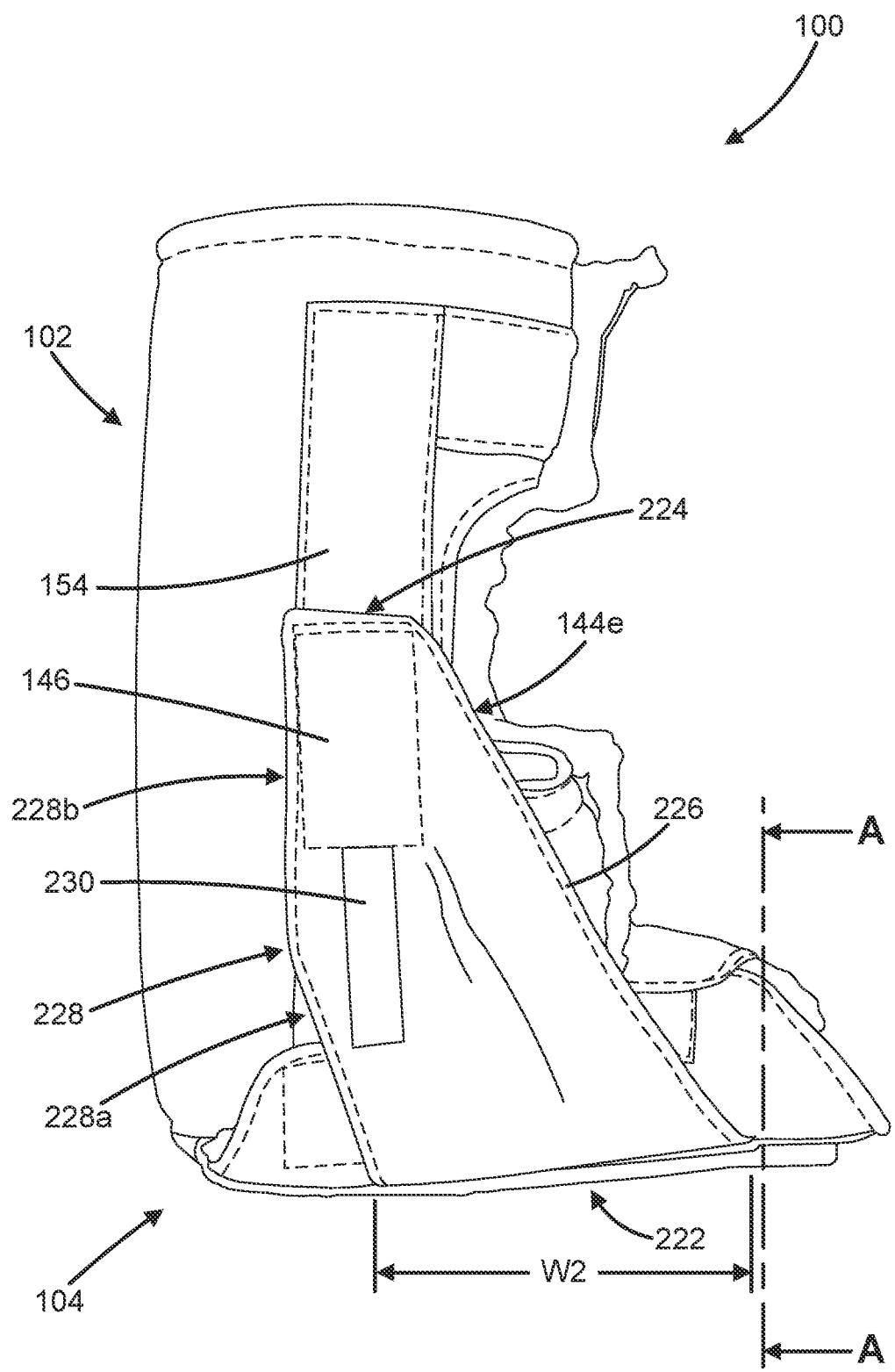
FIG. 14 is a side perspective view of the heel float therapeutic boot shown in FIG. 1.

FIG. 14 is a side perspective view of an example of the wing support structure 106 attached to a heel float therapeutic boot 100. The wing support structure 106 of the heel float therapeutic boot 100 supports the foot in a preferred position. The wing support structure 106 is attached to the heel float therapeutic boot 100 and is configured to be adjustable to obtain the preferred position. The arrangement and configuration of the back side 228 of the wing support structure 106 provides for flexibility of attaching the wing support structure 106 to the loop material 154 that helps place the foot support portion 104 in the proper position. The wing support structure 106 can be placed anywhere along the loop material 154 as desired. The positioning of the wing support structure 106 will vary with each patient. A proper fit can be obtained for any patient from a pediatric size foot up to a man's size 14 foot. The configuration of the wing support structure 106 also provides for easy access to the heel of the foot.

The wing support structure 106 is adjustable to be positioned along the loop material 154. In this example, the wing support structure 106 is adjustable along the lower leg support portion 102 perpendicular to Axis A. Axis A extends longitudinally through the foot support portion 104. The wing support structure 106 has the flexibility to position the foot between 75-110 degrees about axis A. This feature provides for a patient to have the ability to access any part of the bottom of the foot and position the foot as desired. The width W2 of the bottom side 22 of the wing support structure 106 and the configuration of attachment not only helps to keep the foot in an upright position, but it also helps to keep the foot in place so that it is less likely to rotate or migrate around inside of the heel float therapeutic boot 100.

Figure 15:
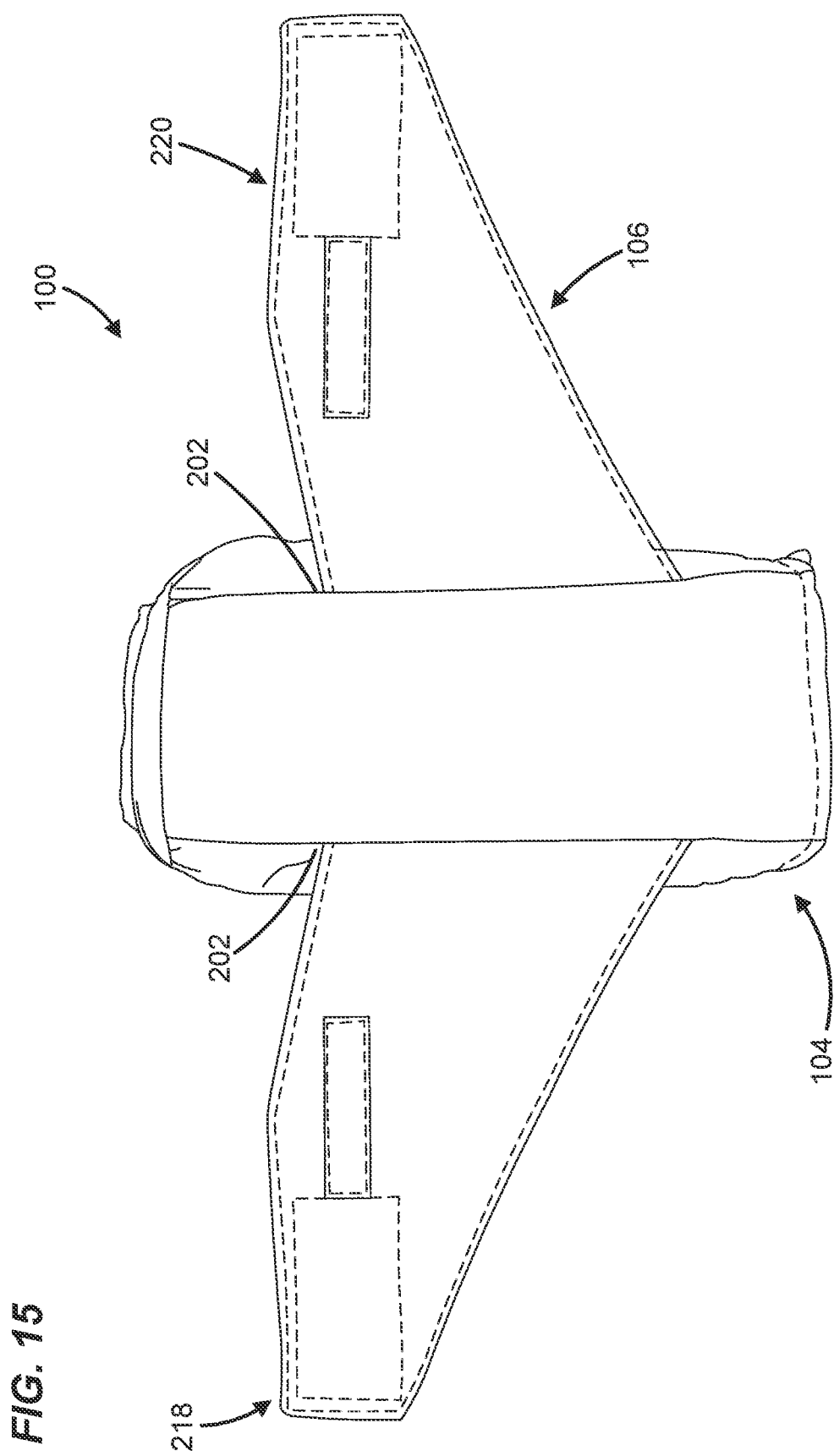
FIG. 15 is a bottom perspective view of the heel float therapeutic boot shown in FIG. 1 with the wing support structure unfastened.
Figure 16:
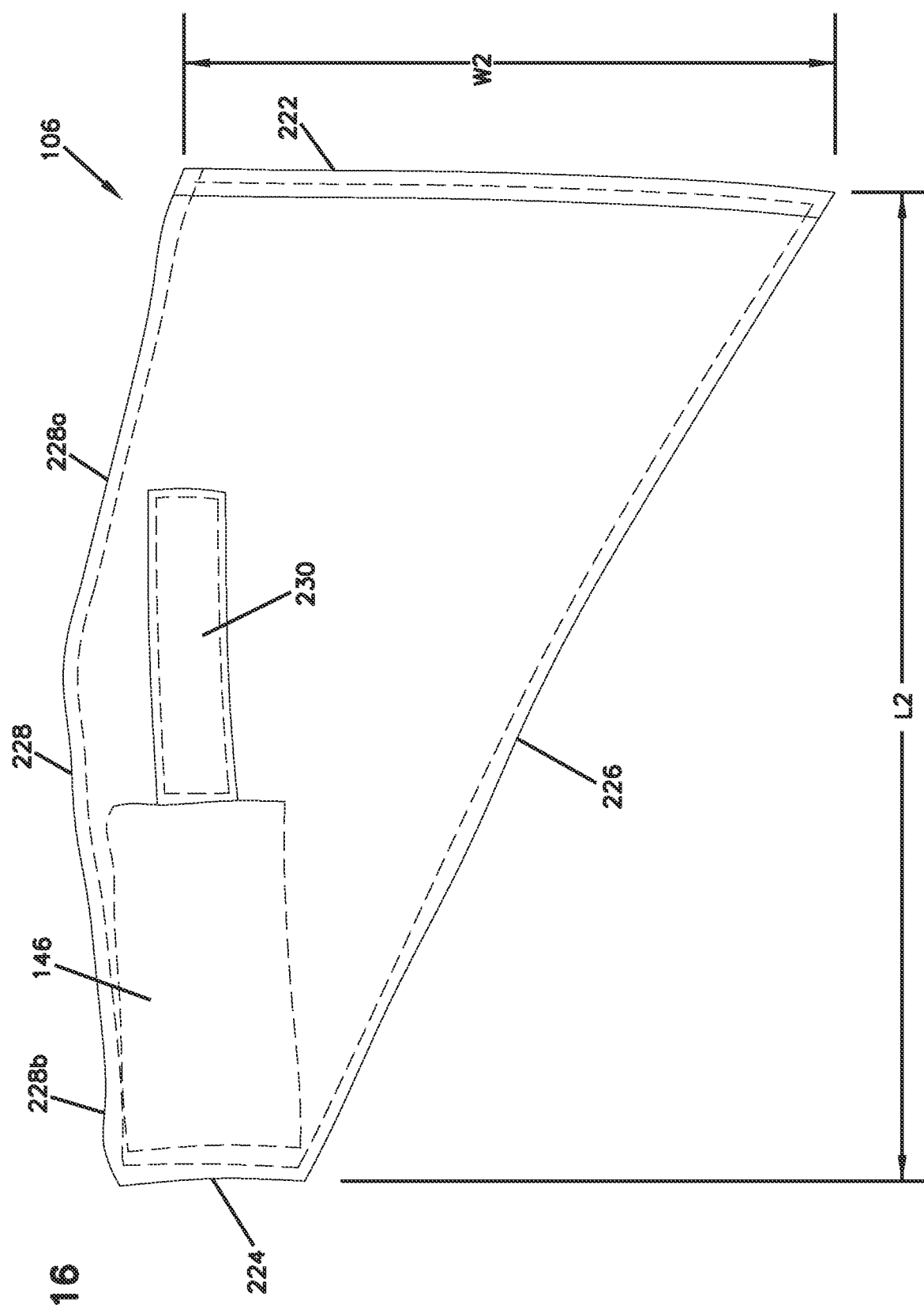
FIG. 16 is an enlarged view of the wing support structure shown in FIG. 15.

FIGS. 15-16 illustrate features of the wing support structure 106.

FIGS. 15-16 are perspective views of the wing support structure 106.

Referring to FIG. 15, the bottom side 222 of the wing support structure 106 is sewn along the longitudinal sides 202 and intersects together with the layers in the foot support portion 104. Portions of the wing support structure 106 extend beyond the sewn area along the longitudinal sides 202 to help prevent the wing support structure 106 from detaching from the foot support portion 104. The bottom side 222 of the wing support structure 106 has a width W2 that extends along a portion of the base 196 of the foot support portion 104. The bottom side 222 of the wing support structure 106 is positioned mostly centered on the base 196. The configuration of the wing support structure 106 eliminates the problem of generating pressure points underneath the foot because no portion of the wing support structure 106 goes across the ball of the foot. The wing support structure 106 is anchored to the sole and helps to spread the pressure points or force across the patient's foot while holding the foot support portion 104 of the heel float therapeutic boot 100 in a desired position. The wing support structure 106 is arranged and configured to keep the foot support portion 104 of the heel float therapeutic boot 100 pulled up or upright.

In the illustrated example, the wing support structure 106 includes a left support wing 218 and a right support wing 220. The left and right support wings 218, 220 are arranged and configured on opposite sides of the heel float therapeutic boot 100. The left and right support wings 218, 220 are each attached to the heel float therapeutic boot 100 along the longitudinal sides 202 in the region of the sole. In the illustrated example, the left and right support wings 218, 220 are permanently fastened to the foot support portion 104. The configuration provides for a wing support structure 106 that is non-adjustable in relation to the foot support portion 104. The wing support structure 106 is adjustably fastenable along the sides of the lower leg support portion 102 (shown in FIG. 14). The wing support structure 106 is wide enough and fixed to the foot support portion 104 to help prevent the foot of a patient from wrapping across the top of the heel float therapeutic boot 100 or popping out underneath the heel float therapeutic boot 100. The wing support structure 106 has a wide area to help disperse any points of pressure, which lowers the likelihood of having a pressure area anywhere in the foot region. Having the wing support structure 106 permanently attached at the sole not only helps to prevent pressure points on the foot but it also helps to eliminate improper positioning of the strap over the foot.

Referring to FIG. 16, the wing support structure 106 includes a bottom side 222, an opposing top side 224, a front side 226, a back side 228, and a loop stripe 230. The wing support structure 106 further includes a length L2 and a width W2.

In the illustrated example, the front side 226 of the wing support structure 106 is angled relative to the back side 228 of the wing support structure 106 such that the top side 224 of the wing support structure 106 is narrower than the bottom side 222 of the wing support structure 106. The front side 226 of the wing support structure 106 being about 9 to 11 inches in length. The top side 224 of the wing support structure 106 includes a hook patch 146 as already described above. The top side 224 is attached to the loop material 154 to position the wing support structure 106 as desired. The top side 224 of the wing support structure 106 being about 1 to 2 inches in length.

In the illustrated example, the back side 228 of the wing support structure 106 is about 9 to 10 inches in length. The back side 228 has an angled portion 228a parallel to the front side 226 of the wing support structure 106. The angled portion 228a is about 4 to 5 inches in length. The angled portion 228a extends from the bottom side 222 of the wing support structure 106. The angled portion 228a forms a perpendicular portion 228b that is perpendicular to the bottom side 222 of the wing support structure 106. The perpendicular portion 228b being about 4 to 5 inches in length. In other embodiments, other shapes and configurations are possible. The left and right support wings 218, 220 are shaped expanding a length and width with respect to the heel float therapeutic boot 100. In other embodiments, other shapes and configurations are possible.

The left and right support wings 218, 220 each include moisture wicking material similar to the overlapping foot member 184. The left and right support wings 218, 220 each have a fastening mechanism 144e. As illustrated in FIG. 14, the left and right support wings 218, 220 are provided with the hook patch 146 and the loop material 154 as the fastening mechanism 144e similar to those described above. As such, the description for the hook patch 146 and the loop material 154 is hereby incorporated by reference in their entirety for the left and right support wings 218, 220.

Figure 17:
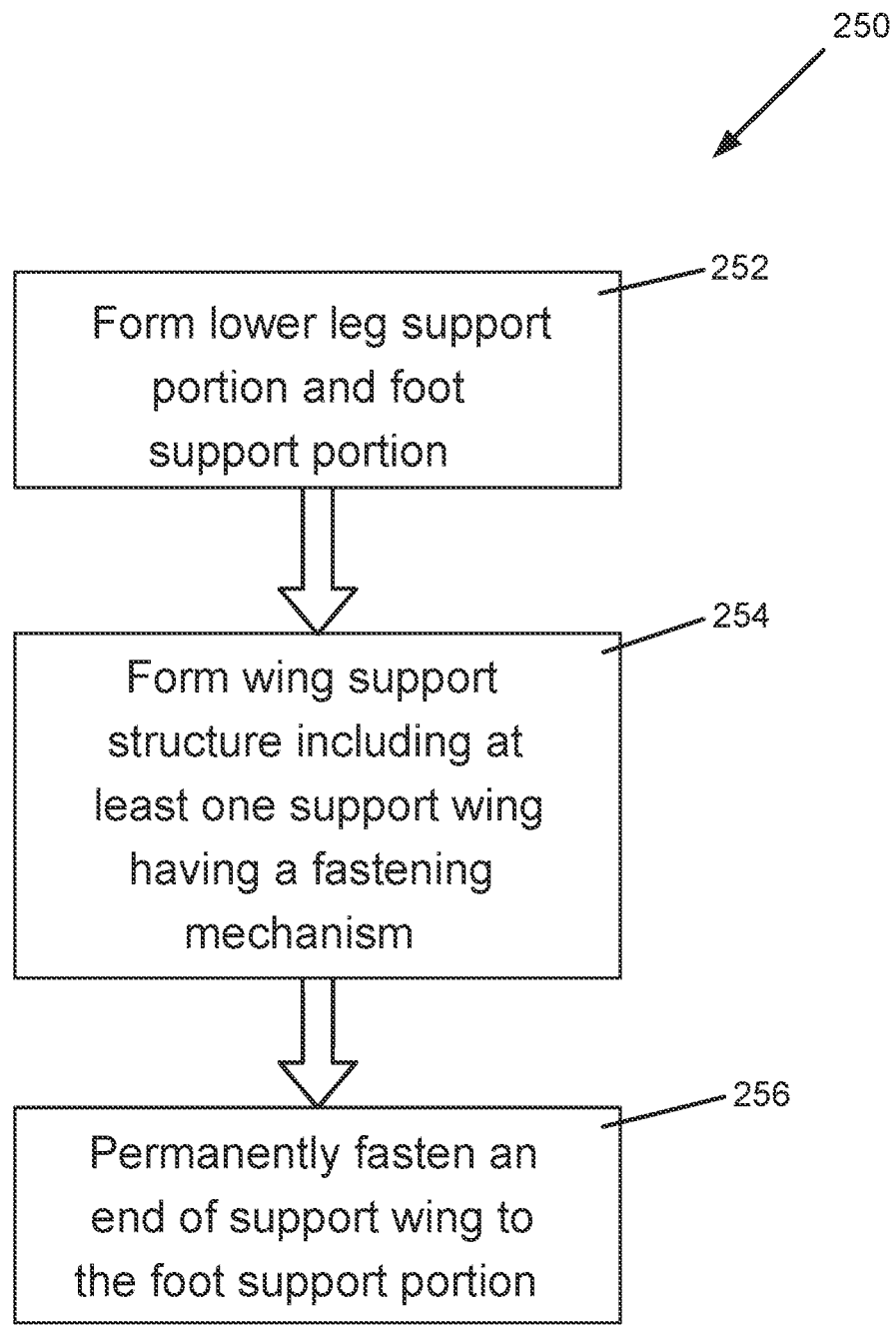
FIG. 17 is a flow chart illustrating a method of making a heel float therapeutic footwear apparatus in accordance with the principles of the present disclosure.

FIG. 17 is a flow chart illustrating an example method 250 of making a heel float therapeutic footwear apparatus 100. In this example, the method 250 includes operations 252, 254, and 256.

The operation 252 is performed to form a lower leg support portion 102 and a foot support portion 104. Examples of the lower leg support portion 102 and the foot support portion 104 are shown and described with reference to FIGS. 1-3. In some embodiments, the foot support portion 104 includes a foot support platform 166. An example of a foot support platform 166 is shown and described with reference to FIG. 11.

The operation 254 is performed to form the wing support structure 106. In some embodiments, the wing support structure 106 includes at least one support wing 106(A,B). In some embodiments, the wing support structure includes a left support wing 106A and a right support wing 106B. The support wings 106 include a first end portion and a second end portion. The second end portion is configured to be adjustably fastened to opposite sides of the lower leg support portion. Examples of the wing support structure 106 and support wings 106A and 106B are illustrated and described in more detail in FIGS. 14-16.

The operation 256 is performed to permanently fasten the first end portion of the support wing 106(A,B) to the foot support portion 104. In some embodiments, operation 256 includes permanently fastening the first end portions of the left and right support wings 106A and 106B to the foot support portion 104. In some embodiments, the one or more support wings 106 are permanently fastened to the foot support platform 166. An example of the fastening operation is sewing with thread. Other fastening operations can also be used, such as described herein. Examples showing the attachment of the wing support structure 106 and support wings 106A and 106B to the foot support portion 104 are shown in FIGS. 1 and 14.

After the heel float therapeutic footwear apparatus 100 has been made, a method of using the heal float therapeutic footwear apparatus 100 can be performed. In one example embodiment, the heel float therapeutic footwear apparatus 100 is arranged on a foot and lower leg of a patient, such as illustrated in FIG. 13. The foot and lower leg are then secured in the heel float therapeutic footwear apparatus 100 using the various panels and fasteners described herein.

Additionally, the second end of one or more of the support wings 106A and 106B are adjustably secured to sides of the lower leg support 102. The heal float therapeutic footwear apparatus 100 securely supports the foot and lower leg in a desired position. The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A heel float therapeutic footwear apparatus comprising:
    a lower leg support portion including a first plurality of layers, the first plurality of layers including at least a fleece material, a heel float cradle, and an exterior fabric, the heel float cradle configured to elevate a heel inside an interior region, wherein the heel float cradle includes an anterior surface that is configured to support a lower leg or calf of a patient to reduce pressure on the heel of the patient, and wherein the heel float cradle is made of foam; and
    a foot support portion extending from the lower leg support portion, the foot support portion including a second plurality of layers, the second plurality of layers includes at least the fleece material, a foot support platform made of foam, and the exterior fabric, wherein the foot support portion extends from the lower leg support portion forming a hinge at the interior region where the heel is configured to be elevated.

2. The heel float therapeutic footwear apparatus according to claim 1, further comprising:
    a wing support structure permanently attached at a first end portion to the foot support portion, and having a second end portion that is adjustably fastenable to a side of the lower leg support portion, wherein the first end portion of the wing support structure is sewn to the foot support portion.

3. The heel float therapeutic footwear apparatus according to claim 2, wherein the wing support structure has a width that extends across part of the foot support portion.

4. The heel float therapeutic footwear apparatus according to claim 2, wherein the wing support structure further comprises a left support wing and a right support wing attached on opposite sides of the foot support portion.

5. The heel float therapeutic footwear apparatus according to claim 2, wherein the wing support structure is connected to the lower leg support portion using a releasable fastener.

6. The heel float therapeutic footwear apparatus according to claim 5, wherein the releasable fastener is a hook and a loop fastener.

7. The heel float therapeutic footwear apparatus according to claim 1, wherein the second plurality of layers further includes a grip material covering the foot support portion.

8. The heel float therapeutic footwear apparatus according to claim 1, wherein the first plurality of layers and the second plurality of layers are at least partially laminated.

9. The heel float therapeutic footwear apparatus according to claim 1, wherein the exterior fabric includes loop material.

10. A heel float therapeutic footwear apparatus comprising:
    a lower leg support portion configured to support a lower leg of a patient, the lower leg support portion including a heel float cradle configured to elevate a heel of the patient when the patient is lying on the patient's back to reduce pressure on the patient's heel, wherein the heel float cradle is made of foam and includes:
        an anterior surface, the anterior surface extending along a longitudinal channel and being configured to support a lower leg or calf of a patient; and
        a cutout region adjacent to a peripheral edge of the anterior surface; and
    a foot support portion connected to and extending from the lower leg support portion; the foot support portion including a foot support platform made of foam, wherein the foot support portion extends from the lower leg support portion forming a hinge in a space where the heel is elevated.

11. The heel float therapeutic footwear apparatus according to claim 10, wherein the foot support platform includes:
    an extended flap portion being configured to align with a base of the foot support portion, the extended flap portion having a proximal end bonded to a recess adjacent the cutout region; and
    flaps extending from opposite sides of the extended flap portion.

12. The heel float therapeutic footwear apparatus according to claim 10, further comprising:
    a wing support structure having a first end portion and a second end portion, the wing support structure permanently attached to the foot support platform at the first end portion, and being adjustably fastenable at the second end portion to a side of the lower leg support portion to adjustably support a position and an angle of the foot support platform with respect to the lower leg support portion;
    wherein the wing support structure further comprises a left support wing and a right support wing attached on opposite sides of the foot support portion, wherein the left support wing and the right support wing are spaced from each other.

13. The heel float therapeutic footwear apparatus according to claim 12, wherein the wing support structure is sewn to the foot support portion.

14. The heel float therapeutic footwear apparatus according to claim 12, wherein the wing support structure is connected to the lower leg support portion using a releasable fastener.

15. The heel float therapeutic footwear apparatus according to claim 10, wherein lower leg support portion includes a first plurality of layers including at least a fleece material, the heel float cradle, and an exterior fabric; and
    wherein the first plurality of layers is at least partially laminated.

16. The heel float therapeutic footwear apparatus according to claim 15, wherein the foot support portion includes a second plurality of layers including at least the fleece material, the foot support platform, and the exterior fabric; and
    wherein the second plurality of layers is at least partially laminated.

17. The heel float therapeutic footwear apparatus according to claim 16, wherein the second plurality of layers further includes a grip material covering the foot support portion.

18. The heel float therapeutic footwear apparatus according to claim 16, wherein the exterior fabric includes loop material.

* * * * *